United States Patent
Barclay et al.

(10) Patent No.: US 9,174,016 B2
(45) Date of Patent: Nov. 3, 2015

(54) HUMIDIFIER FOR A BREATHING SYSTEM

(75) Inventors: Mark W. Barclay, Saxonburg, PA (US); Kenneth E. Cole, New Alexandria, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 535 days.

(21) Appl. No.: 13/000,106

(22) PCT Filed: Jun. 18, 2009

(86) PCT No.: PCT/IB2009/052613
§ 371 (c)(1),
(2), (4) Date: Dec. 20, 2010

(87) PCT Pub. No.: WO2009/156921
PCT Pub. Date: Dec. 30, 2009

(65) Prior Publication Data
US 2011/0100363 A1    May 5, 2011

Related U.S. Application Data

(60) Provisional application No. 61/076,250, filed on Jun. 27, 2008.

(51) Int. Cl.
*A61M 16/16* (2006.01)
*A61M 16/08* (2006.01)
*A61M 16/10* (2006.01)

(52) U.S. Cl.
CPC ........... *A61M 16/16* (2013.01); *A61M 16/0808* (2013.01); *A61M 16/109* (2014.02)

(58) Field of Classification Search
CPC ..................... A61M 16/1045; A61M 16/1075; A61M 16/108; A61M 16/1085; A61M 16/109; A61M 16/1095; A61M 16/14; A61M 16/16; A61M 16/161; A61M 16/162; A61M 16/164; A61M 16/08; A61M 16/0808
USPC ............. 128/203.12, 203.26–203.27, 203.29, 128/204.14, 204.17–204.18
See application file for complete search history.

(56) References Cited

U.S. PATENT DOCUMENTS

| 3,965,894 A | 6/1976 | Fischer |
| 4,417,574 A * | 11/1983 | Talonn et al. ............ 128/205.12 |
| 5,228,436 A * | 7/1993 | Parkin ....................... 128/205.12 |
| 5,655,522 A | 8/1997 | Mechlenburg |
| 6,360,741 B2 | 3/2002 | Truschel |
| 6,401,713 B1 | 6/2002 | Hill |
| 6,467,477 B1 | 10/2002 | Frank |

(Continued)

FOREIGN PATENT DOCUMENTS

| CN | 1375340 A | 10/2002 |
| JP | 06336113 A | 6/1994 |
| JP | 2000337670 A | 12/2000 |

(Continued)

*Primary Examiner* — Rachel Young
(74) *Attorney, Agent, or Firm* — Michael W. Haas

(57) ABSTRACT

An in-line humidifier is disposed along the passageway of a breathing system. The humidifier includes a humidification chamber having a fluid inlet, a fluid outlet, and a reservoir. The humidifier includes a liquid trap which includes a chamber, a fluid inlet in communication with the liquid trap chamber, and a fluid outlet in communication with the liquid trap chamber. The liquid trap is constructed and arranged to discourage liquid from back-flowing from the humidifier to a source of gas.

13 Claims, 4 Drawing Sheets

(56) References Cited

U.S. PATENT DOCUMENTS

| | | | |
|---|---|---|---|
| 6,644,311 B1 | 11/2003 | Truitt | |
| 6,935,337 B2 * | 8/2005 | Virr et al. | 128/203.16 |
| 6,959,710 B2 | 11/2005 | Barnett | |
| 7,111,624 B2 * | 9/2006 | Thudor et al. | 128/203.16 |
| 2010/0043791 A1 * | 2/2010 | McAuley et al. | 128/203.14 |

FOREIGN PATENT DOCUMENTS

| | | |
|---|---|---|
| JP | 2007533344 A | 11/2007 |
| WO | WO02066106 A1 | 8/2002 |
| WO | WO2007019625 A1 | 2/2007 |
| WO | WO2007038690 A2 | 4/2007 |
| WO | WO2008024001 A1 | 2/2008 |

* cited by examiner

HUMIDIFIER FOR A BREATHING SYSTEM

The present invention relates to humidifiers, for example of the in-line type that are used in breathing systems to humidify gas being provided to a patient.

Various breathing systems use in-line humidifiers to humidify a flow of gas being provided to a patient. For example, positive airway pressure (PAP) machines, such as continuous positive airway pressure (CPAP) device provide a continuous positive airway pressure to a patient via a suitable patient interface (e.g., a mask) for various medical reasons (e.g., to treat sleep apnea). Humidifiers are frequently provided between the PAP machine and the patient interface in order to humidify the otherwise relatively-dry flow of gas generated by the PAP machine. Unfortunately, under certain circumstances (e.g., the humidifier being turned upside-down and/or shaken), liquid (e.g., distilled water) in conventional humidifiers can back-flow or splash from the humidifier into the PAP machine, thereby damaging the PAP machine, interfering with its operation, and/or creating problems associated with the build-up of liquid in the PAP machine. In various PAP machines, even a very small amount of liquid back-flow into the machine can damage a sensor within the machine.

One or more embodiments of the present invention provide an in-line humidifier with a liquid trap that discourages liquid from back-flowing through the humidifier's fluid inlet. According to one embodiment of the present invention, the in-line humidifier includes a humidification chamber and a liquid trap. The humidification chamber includes a fluid inlet, a fluid outlet, and a reservoir. The liquid trap includes a chamber, a fluid inlet in fluid communication with the liquid trap chamber, and a fluid outlet in fluid communication with the liquid trap chamber. The fluid outlet of the liquid trap is constructed and arranged to be in fluid communication with the fluid inlet of the humidification chamber. The configuration of the tubings, the chambers, and the tiered arrangement of the humidification chamber and liquid trap provide a series of barriers or obstacles that prevent and/or catch liquid that attempt to flow from the humidifier back into the PAP machine to which the humidifier is connected over a very large range or spatial orientations of the humidifier. That is, the humidifier containing liquid can be moved, turned, oriented, shaken, over a wide range of positions in space with little or none of the liquid exiting the humidification chamber from the gas inlet to the humidifier.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

FIGS. 1-8 illustrate a breathing system 1 according to an embodiment of the present invention. The system 1 and its operation are sequentially described below.

Figure 1:
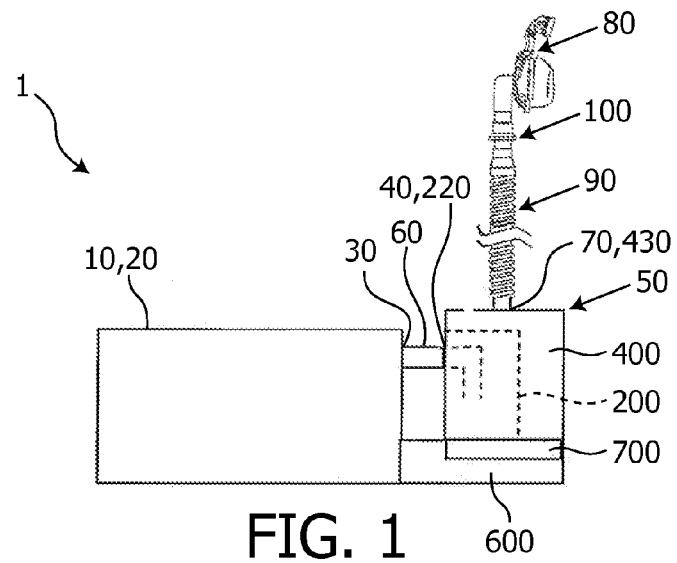
FIG. 1 is diagrammatic front view of a breathing system according to an embodiment of the present invention.
Figure 2:
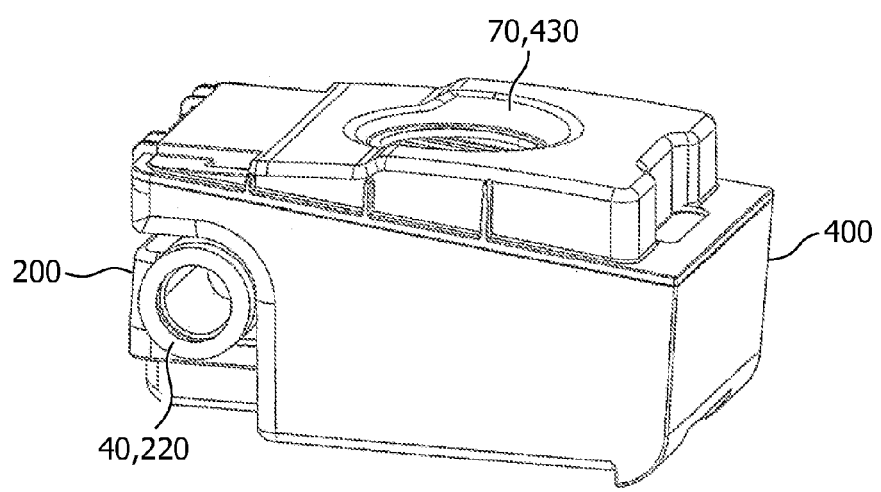
FIG. 2 is a left-side perspective view of a humidification chamber and liquid trap of a humidifier thereof.

As shown in FIG. 1, the system 1 includes a source of gas 10 (also referred to as a pressure generating system), an in-line humidifier 50, and a patient interface 80. Source of gas 10 comprises a PAP machine 20, as is well known in the art (e.g., Respironics' REMstar®, BiPAP®, and SleepEasy® lines of PAP machines). It is be understood that PAP machines, as used herein, refers to any device that generates a flow of gas for delivery to the patient, regardless, for example, of whether flow and/or pressure is constant or varying, the system is invasive or non-invasive, includes a supplement gas such as oxygen, and is single-limb or dual limb. Moreover, according to alternative embodiments of the present invention, a variety of alternative sources of gas 10 may be used as the gas source without deviating from the scope of the present invention (e.g., ventilator, oxygen concentrator, compressed gas tank, etc.) to provide a variety of gases (e.g., air from the ambient environment or a storage container, oxygen-enriched gas, etc.).

A gas outlet 30 of PAP machine 20 fluidly connects to a fluid inlet 40 of humidifier 50 via a suitable passageway (e.g., tubing 60). It should be noted that humidifier 50 can be connected in-line in the gas delivery circuit, which is also referred to as the patient circuit, at any location along that circuit, i.e., humidifier 50 need not be located proximate to the pressure/flow generator or gas source (PAP machine 20).

As shown in FIG. 1, a fluid outlet 70 of humidifier 50 fluidly connects to patient interface 80 via a suitable fluid passageway (e.g., flexible tubing 90). Patient interface 80 may comprise any type of suitable patient interface 80 for directing a flow of gas toward and/or into a patient's airway (e.g., full face mask; nasal mask; total face mask, nasal pillows mask; nasal cannula, intubation tube). In a single-limb pressure support system, which is the type of breathing system shown in FIG. 1, patient interface 80 includes an exhalation port 100 to exhaust a flow of gas to the ambient atmosphere. The present invention contemplates that humidifier 50 can also be used in a dual-limb system that includes an inspiratory limb to deliver a flow of gas to the patient and an expiratory limb to communicate a flow of gas from the patient. In a dual-limb system exhalation port 100 is eliminated.

U.S. Pat. Nos. 5,655,522, 6,360,741, 6,401,713, 6,467,477, 6,644,311, and 6,959,710, the entire contents of which are hereby incorporated by reference, disclose a variety of pressure generating systems, patient interfaces, and/or other parts of breathing systems that may be used as part of one or more embodiments of the present invention.

Humidifier 50 is described below with reference to FIGS. 1-7. As shown in FIG. 1, humidifier 50 comprises a liquid trap 200, a humidification chamber 400, a base 600, and a heater 700. It should be noted that base 600 and heater 700 are optional. For example, liquid trap 200 and humidification chamber 400 can be coupled to pressure generating system 10 directly and can be used without a heater, i.e., as a passive humidifier.

Figure 4:
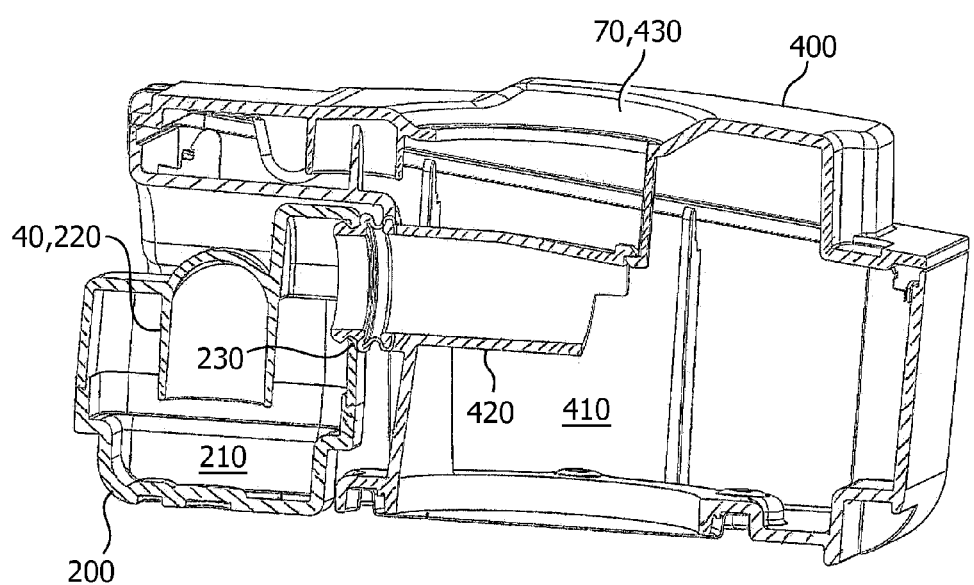
FIG. 4 is a cross-sectional perspective view of the humidification chamber and liquid trap when attached to each other.
Figure 5:
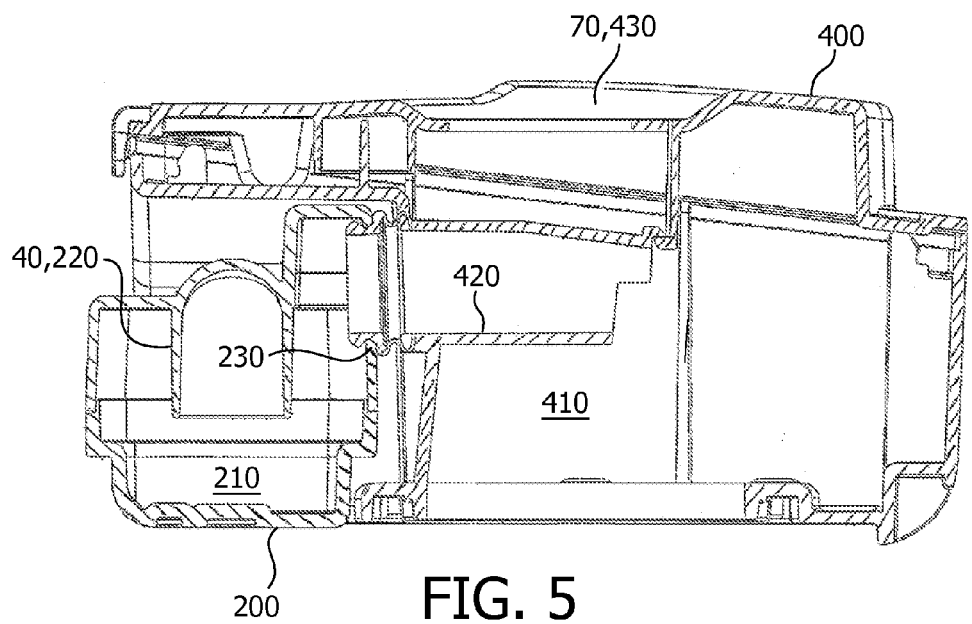
FIG. 5 is a cross-sectional view of the humidification chamber and liquid trap when attached to each other.
Figure 8:
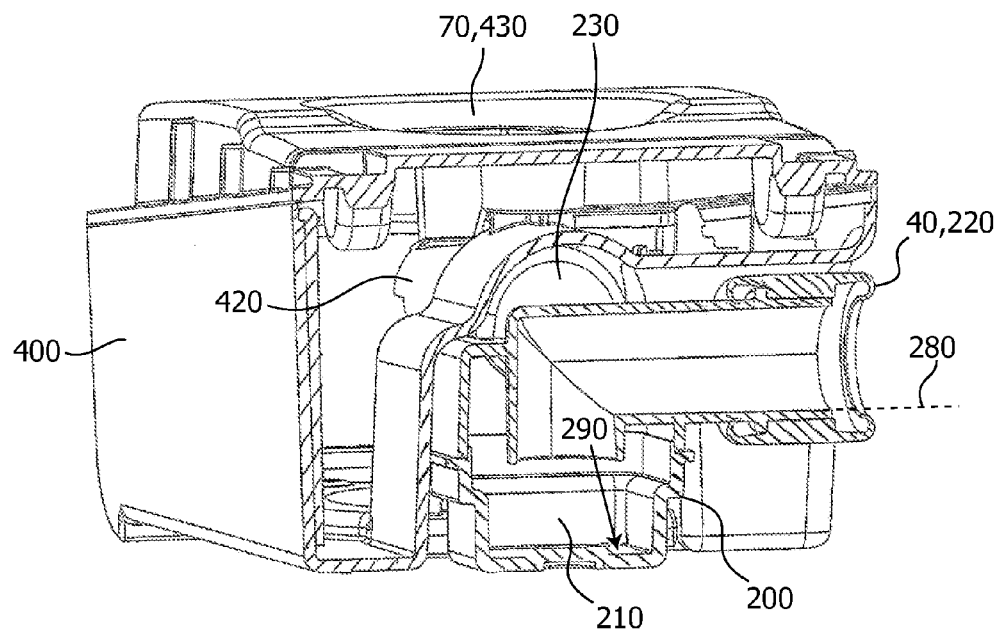
FIG. 8 is a cross-sectional perspective rear view of the humidification chamber and liquid trap when attached to each other.

As shown in FIGS. 4, 5, and 8, liquid trap 200 comprises a chamber 210, a fluid inlet 220 that is in fluid communication with chamber 210 and defines fluid inlet 40 of humidifier 50, and a fluid outlet 230 in fluid communication with chamber 210.

Figure 7:
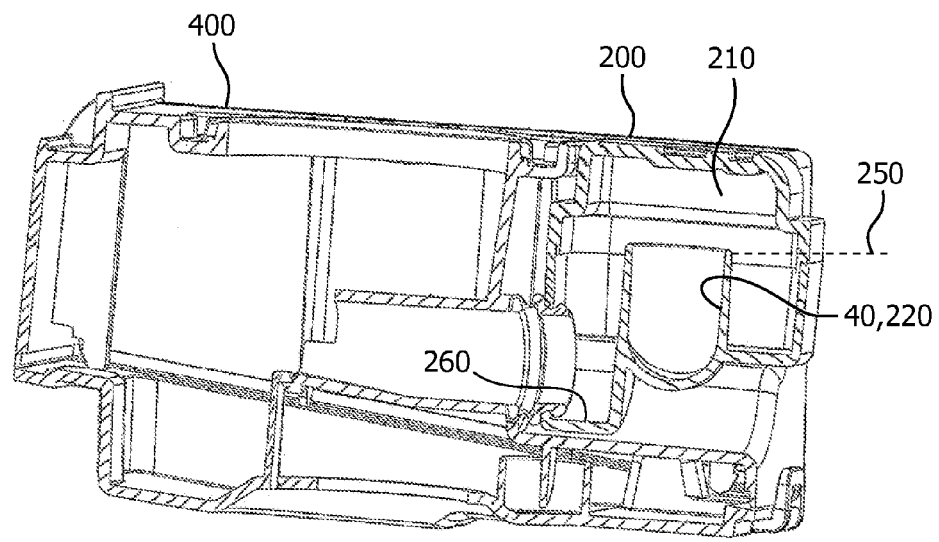
FIG. 7 is a cross-sectional perspective view of the humidification chamber and liquid trap in an upside-down orientation.

As shown in FIGS. 4, 5, 7, and 8, inlet 220 projects inwardly toward a central portion of chamber 210. Consequently, as shown in FIG. 7, when liquid trap 200 is upside-down, liquid trap's fluid inlet 220 has an upside-down spill height 250 that is elevated relative to a low point 260 of an interior of liquid trap's chamber 210. As used herein, the "spill height" of an opening (e.g., inlet, outlet) means the height of liquid within the associated container (e.g., chamber) at which liquid will begin to spill from the container out through the opening. Consequently, when liquid trap 200 is upside-down, liquid tends not to spill out of the liquid trap through fluid inlet 220 unless a liquid level within liquid trap's chamber 210 rises above upside-down spill height 250.

As shown in FIGS. 4, 5, 7, and 8, fluid inlet 220 extends toward an interior of chamber 210, and in an exemplary embodiment to a central portion of chamber 210, such that the liquid trap's fluid inlet's spill height is elevated relative to a low point of an interior of liquid trap's chamber 210 regardless of an orientation of liquid trap 200. For example, when the liquid trap is upright as shown in FIG. 8, a spill height 280 of inlet 220 is elevated relative to a low point 290 within chamber 210. The same is true when liquid trap 200 is on its sides, front, or back. However, spill height of the inlet 220 may be disposed at the low point of chamber 210 in various orientations without deviating from the scope of the present invention.

As shown in FIG. 8, liquid trap 200 has a minimum trap capacity defined by a volume within the liquid trap's chamber disposed below the spill height of liquid trap's fluid inlet 220 when the liquid trap is in an orientation that minimizes said volume.

Humidification chamber 400 has a reservoir 410, a fluid inlet 420 in fluid communication with the reservoir 410, and a fluid outlet 430 that is in fluid communication with reservoir 410 and defines fluid outlet 70 of humidifier 50. In an exemplary embodiment, gas inlet 420 and the walls of humidification chamber 400 are a unitary structure, e.g., formed as single piece of extruded material.

Figure 6:
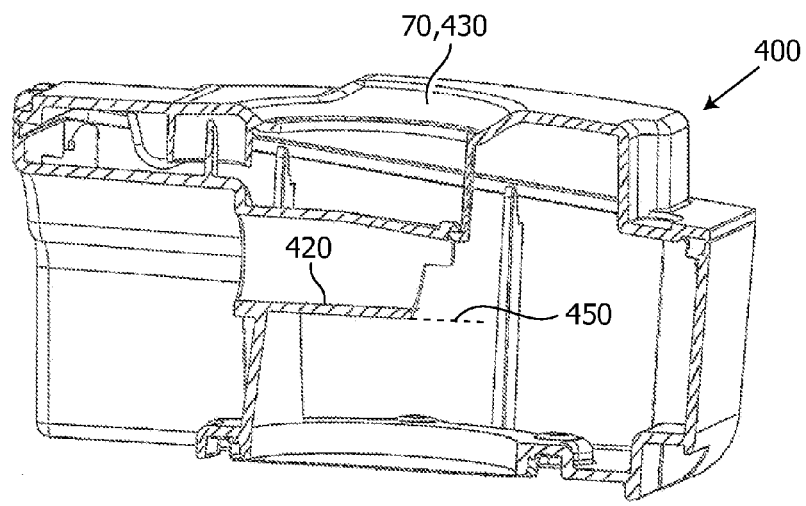
FIG. 6 is a cross-sectional perspective view of the humidification chamber.

As shown in FIG. 6, fluid inlet 420 of humidification chamber 400 defines an upright spill height 450 such that liquid tends to spill out of humidification chamber 400 through fluid inlet 420 thereof if the humidification chamber is upright and a liquid level within humidification chamber's reservoir 410 rises above spill height 450. Reservoir 410 has a liquid capacity defined by a volume within the interior of humidification chamber 400 disposed below spill height 450 of fluid inlet 420 when humidification chamber 400 is in an upright position.

As shown in FIG. 6, fluid inlet 420 projects into humidification chamber 400 so as the fluid inlet's spill height is elevated relative to a low point of reservoir 410 regardless of an orientation of humidification chamber 400. Such elevation tends to discourage liquid from flowing from humidification chamber 400 to liquid trap 200 when the disposed in non-upright orientations (e.g., sideways, upside-down, etc.). Humidification chamber 400 has a minimum humidification chamber capacity defined by a volume within the humidification chamber disposed below the spill height of the fluid inlet 420 when the humidification chamber is in an orientation that minimizes said volume.

Figure 3:
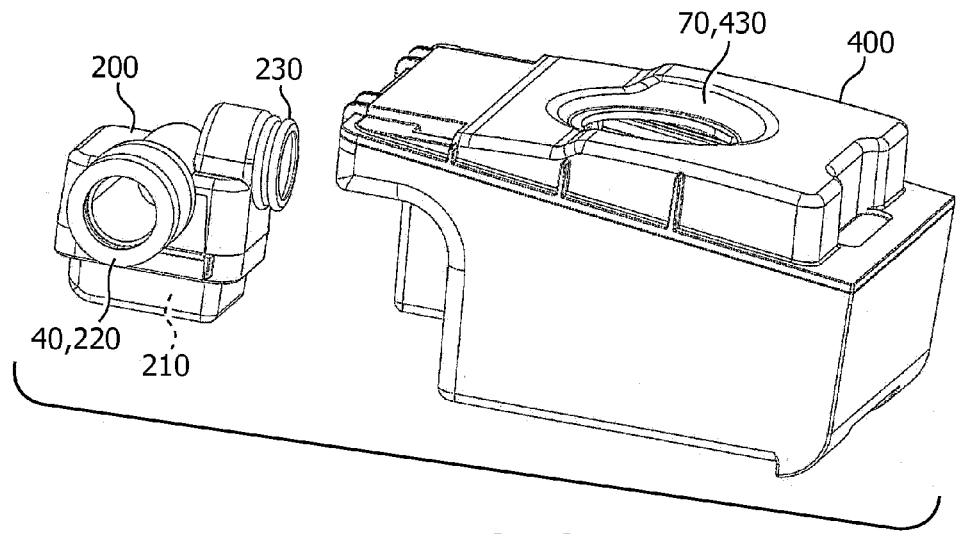
FIG. 3 is a left-side perspective view of the humidification chamber and liquid trap when detached from each other.

As shown in FIGS. 2-7, humidification chamber 400 and liquid trap 200 are constructed and arranged to be releasably connected to each other (see FIGS. 2, 4, 5, 7) and detached from each other (see FIGS. 3, 6). When humidification chamber 400 and liquid trap 200 are connected to each other, fluid outlet 230 of liquid trap 200 engages and is in fluid communication with fluid inlet 420 of humidification chamber 400. As shown in FIGS. 3 and 4, fluid outlet 230 of liquid trap 200 and fluid inlet 420 of humidification chamber 200 include mating portions that provide at least a partial seal between liquid trap 200 and humidification chamber 400 when they are connected to each other. These same mating portions (or other discrete portions) may also provide a physical connection that tends to keep humidification chamber 400 and liquid trap 200 connected to each other.

As shown in FIG. 1, liquid trap 200 releasably connects to humidifier base 600. However, liquid trap 200 may alternatively be permanently attached to base 600 (e.g., via integral formation) without deviating from the scope of the present invention.

Base 600 releasably attaches to the PAP machine 20. However, base 600 may alternatively be permanently attached to the PAP machine 20 (e.g., via integral formation) without deviating from the scope of the present invention. The attachment (releasable or not) between base 600 and PAP machine 20 facilitates secure connection between the PAP machine's gas outlet 30 and inlet 220 of liquid trap 200 (e.g., via suitable tubing 60). Alternatively, humidifier 50 may comprise a stand-alone unit that connects to the PAP machine 20 via a suitable passageway (e.g., flexible tube) without use of base 600.

When liquid trap 200 is attached to base 600 and humidification chamber 400 is attached to liquid trap 200, humidification chamber 400 also attaches to base 600 such that the base at least partially supports the humidification chamber. Again, it should be understood that the present invention contemplates omitting base 600 in favor of attaching liquid trap 200, humidification chamber 400, or both to the housing of the pressure generating system.

As shown in FIG. 1, heater 700 mounts to base 600 and is positioned relative to reservoir 410 of humidification chamber 400 so as to heat liquid therein to facilitate evaporation of the heated liquid and humidification of the gas passing through humidification chamber 400. Alternatively, heater 700 may be incorporated into humidification chamber 400, itself, without deviating from the scope of the present invention.

If base 600 is attachable to PAP machine 20, the PAP machine and heater 700 may be jointly powered (e.g., via a common electrical plug or battery). According to alternative embodiments of the present invention, heater 700 may be replaced with any other suitable mechanism for enhancing humidification of the gas passing through humidification chamber 400 (e.g., ultrasonic atomizer; humidification via gas entering the chamber underneath the liquid such that resulting bubbles tend to be humidified) or omitted altogether.

Hereinafter, operation of system 1 is described. Prior to use, a user detaches humidification chamber 400 from system 1 and fills it (via fluid outlet 430) to a desired level with a suitable humidification liquid (e.g., distilled water). As shown in FIG. 6, spill height 450 of fluid inlet 420 of humidification chamber 400 tends to prevent overfilling because humidification liquid will spill out through inlet 420 if the liquid exceeds the liquid capacity of humidification chamber 400.

The user then attaches chamber 400 to liquid trap 200 and remainder of system 1 and turns the system on. As shown in FIG. 1, PAP machine 20 directs a flow of gas into humidification chamber 400 via the PAP machine's fluid outlet 30, tubing 60, liquid trap's fluid inlet 40, 220, liquid trap's chamber 210, liquid trap's fluid outlet 230, and humidification chamber's fluid inlet 420. Heater 700 heats the liquid. The liquid evaporates into the gas stream within humidification chamber 400. The gas pressure directs the humidified gas to patient interface 80 via the humidification chamber's fluid outlet 430 and tubing 90, thereby providing a flow of humidified gas to the patient.

If humidifier 50 is inadvertently knocked over or otherwise overturned during use or when otherwise containing liquid (e.g., upside-down as shown in FIG. 7, sideways, etc.), humidification chamber 400 is designed to reduce or eliminate back-flow of the liquid into liquid trap 200. Humidification chamber 400 is configured and sized to prevent liquid from flowing or splashing back through fluid inlet 420 and into liquid trap 200. For example, humidification chamber is provided with a shelf area that will contain fluid in the event the humidification chamber 400 is tilted such that fluid inlet 420 is vertical with the opening of inlet 420 at the lowermost portion of the chamber.

In a worst case scenario (e.g., with outlet 430 plugged and the humidification chamber in an orientation that minimizes its capacity), a certain amount of liquid (e.g., a volume by which the liquid capacity of the humidification chamber 400 exceeds the humidification chamber's minimum humidification chamber capacity) may back-flow into liquid trap 200 via fluid inlet 420 of humidification chamber 400 and fluid outlet 230 of liquid trap 200. The above-discussed spill height and liquid trap capacity of liquid trap 200 helps the trap to trap all or most of such liquid, thereby limiting and/or preventing liquid from further back-flowing into PAP machine 20.

To help ensure that liquid trap 200 has the capacity to trap all or most of the liquid entering it, the liquid trap's minimum trap capacity may exceed a volume by which the liquid capacity of the humidification chamber 400 exceeds the minimum humidification chamber capacity. According to various embodiments of the present invention, the minimum trap capacity is at least $1/20$, $1/10$, $1/8$, $1/5$, $1/4$, $1/3$, $1/2$, $2/3$, and/or $3/4$ as large as the liquid capacity of the humidification chamber 400. According to various embodiments of the present invention, the minimum humidification chamber capacity is at least $1/20$, $1/10$, $1/8$, $1/5$, $1/4$, $1/3$, $1/2$, $2/3$, and/or $3/4$ as large as the liquid capacity of the humidification chamber 400. According to various embodiments of the present invention, the minimum humidification chamber capacity is at least $1/50$, $1/30$, $1/20$, $1/10$, $1/8$, $1/5$, $1/4$, $1/3$, $1/2$, $2/3$, and/or $3/4$ as large as a total volume within the humidification chamber 400.

According to one or more embodiments of the present invention, the tiered use of back-flow-resisting inlets 220, 430 in liquid trap 200 and humidification chamber 400 provides improved resistance to liquid back-flow into PAP machine 20 under a variety of atypical circumstances (e.g., a combination of one or more of shaking of the system 1 which can cause splashing of the liquid, overturning of the system 1, etc.). Moreover, according to one or more embodiments of present invention, the tiered use of liquid trap 200 and humidification chamber 400 enables an overall reduction in the space required for humidifier 50, while still maintaining a high level of resistance to liquid back-flow.

In short, the configuration of the tubings, the chambers, and the tiered configuration of the humidification chamber and liquid trap provide a series of barriers or obstacles that prevent and/or catch liquid that attempt to flow from the humidifier back into the PAP machine to which the humidifier is connected over a very large range or spatial orientations of the humidifier. That is, the humidifier containing liquid can be moved, turned, oriented, shaken, over a wide range of positions in space with little or none of the liquid exiting the humidification chamber from the gas inlet to the humidifier.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An in-line humidifier comprising:
   a humidification chamber having a fluid chamber inlet, a fluid chamber outlet, a chamber interior, a central chamber portion, and a reservoir configured to hold a liquid, and wherein the fluid chamber inlet projects inwardly into the humidification chamber toward the central chamber portion; and
   a liquid trap comprising a trap chamber, a fluid trap inlet in fluid communication with the trap chamber and a source of gas, and a fluid trap outlet in fluid communication with the trap chamber, and a central trap portion, wherein the fluid trap outlet is constructed and arranged to be in fluid communication with the fluid chamber inlet such that liquid back-flowing from the reservoir of the humidification chamber through the fluid chamber inlet is trapped in the liquid trap,
   wherein the fluid trap inlet projects inwardly into the trap chamber toward the central trap portion,
   wherein the fluid trap inlet maintains a non-zero trap spill liquid level regardless of humidifier orientation such that the trap chamber holds some liquid no matter how the liquid trap is oriented,
   wherein the fluid trap inlet is constructed and arranged to be in fluid communication with the source of gas such that liquid up to the non-zero trap spill liquid level in the trap chamber of the liquid trap is prevented from back-flowing through the fluid trap inlet,
   wherein the fluid chamber inlet has a non-zero chamber spill liquid level regardless of humidifier orientation such that the fluid chamber holds some liquid no matter how the humidification chamber is oriented, and
   wherein the fluid chamber inlet is constructed and arranged such that liquid up to the non-zero chamber spill liquid level in the humidification chamber is prevented from back-flowing through the fluid chamber inlet no matter how the humidification chamber is oriented, and
   the humidification chamber and liquid trap are constructed and arranged to be releasably connected to each other for disconnection from each other while keeping the humidification chamber intact and while keeping the liquid trap intact.

2. The humidifier of claim 1, wherein the fluid trap outlet of the liquid trap is connected to and in fluid communication with the fluid chamber inlet of the humidification chamber.

3. The humidifier of claim 1, wherein the in-line humidifier has multiple sides, wherein the non-zero trap spill liquid level of the liquid trap is a non-zero spill liquid level when the in-line humidifier is oriented upright, upside-down, or on either one of the multiple sides of the in-line humidifier, and wherein the non-zero chamber spill liquid level of the humidification chamber is a non-zero spill liquid level when the in-line humidifier is oriented upright, upside-down, or on either one of the multiple sides of the in-line humidifier.

4. The humidifier of claim 1, wherein:
when the humidification chamber and liquid trap are connected to each other, the fluid trap outlet of the liquid trap engages and is in fluid communication with the fluid chamber inlet of the humidification chamber.

5. The humidifier of claim 4, wherein the humidification chamber has a minimum liquid capacity defined by a volume within the humidification chamber disposed below the non-zero chamber spill liquid level of the humidification chamber no matter how the humidification chamber is oriented.

6. The humidifier of claim 5, wherein the liquid trap has a non-zero minimum trap capacity defined by a volume within the trap chamber of the liquid trap disposed below the non-zero trap spill liquid level when the liquid trap is in an orientation that minimizes said volume, wherein the non-zero minimum trap capacity is at least 1/20 of the minimum liquid capacity of the humidification chamber.

7. The humidifier of claim 1, wherein, responsive to the liquid trap being upside-down:
(a) the fluid trap inlet of the liquid trap has a non-zero upside-down spill liquid level regardless of humidifier orientation such that the trap chamber holds some liquid no matter how the liquid trap is oriented, and
(b) liquid in the trap chamber tends not to spill out of the liquid trap through the fluid trap inlet unless a liquid level within the trap chamber of the liquid trap rises above the non-zero upside-down spill liquid level.

8. The humidifier of claim 1, further comprising a heater positioned relative to the reservoir to heat liquid disposed in the reservoir.

9. The humidifier of claim 1, further comprising a patient interface in fluid communication with the fluid chamber outlet of the humidification chamber.

10. The in-line humidifier of claim 1, further comprising the source of gas, wherein the source of gas is arranged to be in fluid communication with the fluid trap inlet of the liquid trap.

11. The humidifier of claim 1, wherein the fluid trap inlet and the fluid trap outlet face different directions.

12. The humidifier of claim 1, wherein the fluid trap inlet forms an elbow-shaped flow path such that the portion of fluid trap inlet projecting inwardly towards the central portion of the fluid trap chamber is perpendicular to the portion of fluid trap inlet in communication with the gas source.

13. An in-line humidifier having multiple sides, the in-line humidifier comprising:

a humidification chamber having a fluid chamber inlet, a fluid chamber outlet, a chamber interior, a central chamber portion, and a reservoir configured to hold a liquid, and wherein the fluid chamber inlet projects inwardly into the humidification chamber toward the central chamber portion; and a liquid trap comprising a trap chamber, a fluid trap inlet in fluid communication with the trap chamber and a source of gas, and a fluid trap outlet in fluid communication with the trap chamber, and a central trap portion, wherein the fluid trap outlet is constructed and arranged to be in fluid communication with the fluid chamber inlet such that liquid back-flowing from the reservoir of the humidification chamber through the fluid chamber inlet is trapped in the liquid trap, wherein the fluid trap inlet projects inwardly into the trap chamber toward the central trap portion, wherein the fluid trap inlet has a non-zero trap spill liquid level regardless of humidifier orientation such that the trap chamber holds some liquid no matter how the in-line humidifier is balanced on any of the sides of the in-line humidifier, wherein the fluid chamber inlet has a non-zero chamber spill liquid level regardless of humidifier orientation such that the fluid chamber holds some liquid no matter how the in-line humidifier is balanced on any of the sides of the in-line humidifier, wherein the fluid chamber inlet is constructed and arranged such that liquid up to the non-zero chamber spill liquid level in the humidification chamber is prevented from back-flowing through the fluid chamber inlet no matter how the in-line humidifier is balanced on any of the sides of the in-line humidifier, and wherein the humidification chamber and liquid trap are constructed and arranged to be releasably connected to each other for disconnection from each other while keeping the humidification chamber intact and while keeping the liquid trap intact.

* * * * *